United States Patent

Narayanan et al.

[11] Patent Number: 6,096,345
[45] Date of Patent: Aug. 1, 2000

[54] COMPOSITION OF AN ACTIVE COMPONENT AND FREE FLOWING PARTICLES OF A POLYSACCHARIDE MATRIX HAVING SIGNIFICANTLY IMPROVED WATER DISPERSIBILITY AND STABILITY IN AQUEOUS SOLUTIONS

[75] Inventors: Kolazi S. Narayanan; Ronald H. Goehner, Jr.; James F. Curry, all of Wayne, N.J.

[73] Assignee: ISP Investments Inc., Wilmington, Del.

[21] Appl. No.: 09/010,642

[22] Filed: Jan. 22, 1998

[51] Int. Cl.[7] .............................. A01N 25/14; A61K 9/14; A61K 47/32
[52] U.S. Cl. ........................ 424/501; 424/499; 428/402
[58] Field of Search .................................. 424/486, 499, 424/501, 409; 514/951–52; 428/402; 71/64.01, 64.13, DIG. 1

[56] References Cited

U.S. PATENT DOCUMENTS

| | | |
|---|---|---|
| 5,209,922 | 5/1993 | Mgrianos et al. . |
| 5,242,684 | 9/1993 | Merianos . |
| 5,639,710 | 6/1997 | Lo et al. . |
| 5,672,353 | 9/1997 | Narayanan . |
| 5,698,211 | 12/1997 | Narayanan . |

*Primary Examiner*—Edward J. Webman
*Attorney, Agent, or Firm*—Marilyn J. Maue; William J. Davis; Walter Katz

[57] ABSTRACT

This invention relates to a composition containing an active chemical and a particulate polysaccharide matrix having improved water dispersibility and dispersion stability in aqueous solutions by the incorporation of a copolymer of a N-vinyl lactam monomer and a hydrophobic comonomer. The improved properties of the matrix promotes its use as a dispersing agent in a wide variety of formulations where soil and skin substantivity or sustained release of the active chemical is required, as in pharmaceutical, pre- and post-emergent agrochemical and cosmetic formulations. The invention also pertains to the preparation and use of formulations based on the use of polysaccharide/copolymer matrix of this invention.

20 Claims, 1 Drawing Sheet

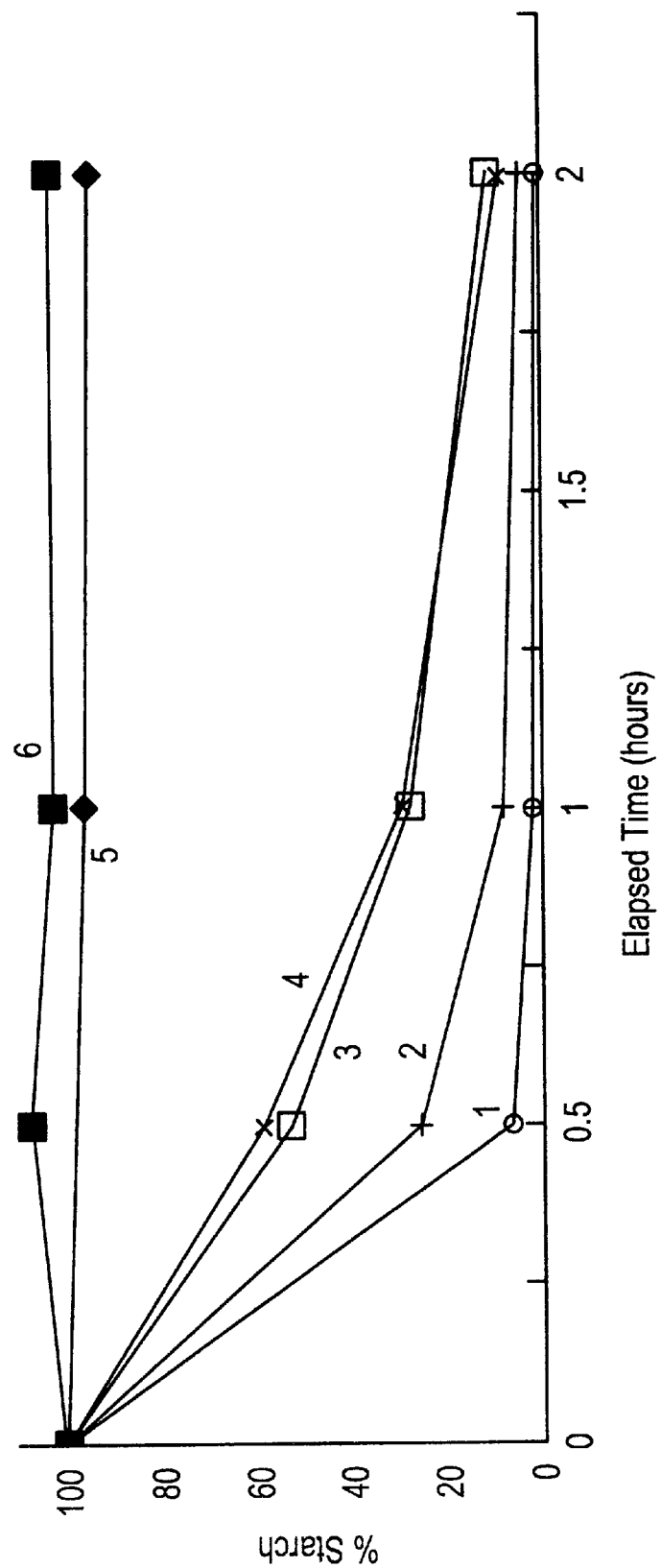

COMPOSITION OF AN ACTIVE COMPONENT AND FREE FLOWING PARTICLES OF A POLYSACCHARIDE MATRIX HAVING SIGNIFICANTLY IMPROVED WATER DISPERSIBILITY AND STABILITY IN AQUEOUS SOLUTIONS

BACKGROUND OF THE INVENTION

Polysaccharide particles, such as starch granules, have been proposed as suitable fillers and tabletting aids for active chemicals in various formulations. However, such dry, free flowing compositions are objectionably unstable in aqueous solutions unless augmented with a significant amount of a dispersion additive, such as cyclodextrin or polyvinylpyrrolidone as described in European Patent Application No. 487,774 A1. Nevertheless, even in the presence of such additives, the dispersibility of the starch component is not materially improved and soil substantivity to prevent leaching into ground water is well below standard and safe requirements.

Accordingly, it is a goal of this invention to overcome the above deficiencies by achieving a naturally occurring polysaccharide composition, particularly a starch composition, having greatly improved stable dispersibility, soil substantivity and leach inhibition of an active agrochemical into ground water.

It is also an object of this invention to provide a highly stable, dispersed aqueous compositions of polysaccharide matrix and an active cosmetic, pharmaceutical or agrochemical compound having high substrate substantivity and sustained release properties for the active chemical.

Yet another object is to provide an ecologically safe and biodegradable matrix for an active biochemical.

These and other objects and advantages of the invention will become apparent from the following description and disclosure.

THE INVENTION

In accordance with the present invention there is provided a free flowing granular composition comprising an active agricultural, cosmetic or pharmaceutical chemical uniformly dispersed on a matrix of naturally occurring or modified polysaccharide particles infused with a copolymer of excess N-vinyl lactam monomer and a minor amount of a water insoluble comonomer. The present copolymer can be optionally crosslinked up to 2% with conventional polyfunctional crosslinking agents such as a polyolefin, polyacrylate, polyalkenyl ether, ethyledinevinyl pyrrolidone, divinylimidazolidone and the like.

The N-vinyl lactam monomer of the present invention is a cyclic amide containing from 4 to 6 ring carbon at oms and which is optionally substituted on the ring with lower alkyl of 1 to 4 carbon atoms. The lactam component of the copolymer also includes mixtures of such N-vinyl lactams. Representative examples of monomer are N-vinyl pyrrolidone, N-vinyl caprolactam, N-vinyl methyl pyrrolidone, N-vinyl ethyl pyrrolidone, N-vinyl methyl caprolactam and the like. Of these monomers, N-vinyl pyrrolidone and mixtures of N-vinyl pyrrolidone and N-vinylcaprolactam are preferred.

The hydrophobic comonomer of the copolymer is a polymerizable compound containing an olefinically unsaturated group, preferably a terminal unsaturated group, and is most preferably an oxygen-containing comonomer. The comonomer as well as the lactam monomer, can be quaternized or non-quaternized for the purposes of this invention, including mono-, di- and tri-lower alkyl ammonium halide salts, halide salts, sulfonate salts and phosphate salts. Examples of other suitable hydrophobic compounds include the lower alkylamino lower alkyl acrylates and methacrylates, $C_4$ to $C_8$ $\alpha$-olefins, lower alkyl vinyl ethers, maleic acid and inorganic salts of said acid, N-vinyl imidazolone, N-vinyl imidazol and mixtures of these compounds as the comonomer species of the invention, such as for example mixtures of N-vinyl imidazolone or N-vinyl imidazol with dimethylamino ethyl methacrylate. Of the above comonomers, alkylamino alkylmethacrylates, particularly dimethylamino lower alkyl methacrylate and dimethylamino lower alkyl methacrylamide are preferred and the ethyl and propyl methacrylate and methacrylamide are particularly preferred.

The concentration of hydrophilic lactam component with respect to hydrophobic component in the copolymer can vary between about 60 and about 98.5 wt. %, and is preferably between about 70 and about 95 wt. %. The weight ratio of hydrophilic to hydrophobic monomer is preferably between about 4:1 and about 8:1. In this invention, the presence of the hydrophobic monomer component is critical for providing the improved soil, hair or skin substantivity desired in the matrix product when applied in aqueous solution. The hydrophobic comonomer also contributes to the improved dispersibility of the matrix/active mixture. Specifically, the polysaccharide, e.g. starch, when combined with the copolymer of this invention, has an altered tertiary structure in which the intramolecular hydrogen bonding, normally present in the unaltered state, is disrupted by the introduction of hydrophobic monomer units which interact with the hydrophobic segment of the starch; thus, exposing the hydrophilic segment of the copolymer for hydrogen bonding with water. Consequently, intramolecular bonding is inhibited and replaced by hydrogen bonding with water which is responsible for the significantly improved dispensability of the present matrix composition.

The matrices of the invention contain between about 5 and about 95 wt. % polysaccharide, preferably between about 15 and about 85 wt. % polysaccharide, with respect to copolymer, although a concentration of between 45 and 55 wt. % polysaccharide is most preferred.

The polysaccharides of the present invention are in the form of free flowing particles having an average diameter of from about 10 to about 350 microns ($\mu$), preferably from 15 to 200$\mu$. Suitable polysaccharides are naturally occurring and modified forms thereof which include cornstarch, potato starch, oxidized starches, methyl cellulose hydroxy propyl cellulose, calcium carboxycellulose and other types generally regarded as water insoluble or only slightly miscible with water. The infusion of the copolymer in the polysaccharide reduces its hydrophobicity and promotes dispersibility of the matrix in an aqueous medium to provide liquid sprays of up to 20% suspended solids which are stable for extended periods of up to several days. Particularly, the use of copolymer in the polysaccharide, e.g. starch, is capable of increasing the dispersibility of the later in aqueous solution up to ten fold in some cases and generally provides a dispersibility improvement between 10 and 90%, depending upon the copolymer selected for infusion.

The modified matrix of the present invention, because of its hydrophobic-hydrophilic moieties, provides compatibility with a wide variety of conventional agrochemical agents including plant growth regulants, fertilizers, pre- and post-emergent herbicides, pesticides, fungicides, nematocides, etc. as well as topical pharmaceutical chemicals and personal care agents for skin and hair conditioning, such as creams and lotions for treating skin disorders, e.g. acne, denture adhesives, mouth washes, tooth whiteners, shampoos, hair sprays, sunscreens, moisturizers, toning agents, defoliating agents, depilatating agents, hair and skin bleaching agents, hair dyes, soaps and the like and commercial laundry detergents and disinfectants. Theoretically, the concentration of the active component can be employed at about the recommended dosage, however because of the resistance to leaching and the improved substrate substantivity provided by the present matrix, somewhat smaller dosages can be effective. Generally, the weight ratio of active component to matrix is between about 1:0.1 and about 1:10, preferably between about 1:0.5 and about 1:5, on a dry basis. Examples of specific agriculturally active chemicals suitably employed herein are disclosed in columns 3 through 8 of U.S. Pat. No. 5,176,736, issued January, 1993, which agrochemicals are incorporated herein by reference.

For active components having a low dispersibility in water, the present matrix composition preferably contains from about 1 to about 20 wt. of an oxygen containing dispersant aid, based on 100% active. Such dispersant aids include lignin sulfonate, naphthalene sulfonate/ formaldehyde condensate, sodium $C_{10}$ to $C_{14}$ succinate or sulfate, such as sodium lauryl succinate or sodium lauryl sulfate, the sodium salts of ethoxylated acrylates or methacrylates, lower alkyl vinyl ether/maleic acid half ester salts, naphthalene sulfonate/formaldehyde condensate, polyanionic polymers such as acrylates, and other conventional dispersant aids conventionally employed for the active pharmaceutical, agricultural or personal care chemicals.

Starch has been used as a binder/disintegrant in solid, water dispersible granules or solid compositions which provide sustained release of the active chemical as disclosed in U.S. Pat. No. 4,911,952. However, the patented process for preparing the granules containing the active component requires starch pregelatinization and extrusion of the starch and active at high temperatures and pressures which automatically excludes the incorporation of temperature sensitive active ingredients. Conversely, the present process with the modified polysaccharide eliminates pregelatinization and enables extrusion of active/matrix at ambient temperature, as illustrated in Examples 7–9 which follow.

More specifically, the free flowing matrix/active solids of this invention are prepared under ambient conditions by forming a 10 to 80% aqueous slurry of active/dispersant mixture to which is added the polysaccharide/copolymer in the concentrations discussed above. The polysaccharide/ copolymer is formed by intimate mixing of the copolymer, polysaccharide and from about 20 to about 80 wt. % water until a uniform composition is attained. This composition can be predried and ground to the desired particle size or the polysaccharide in a desired particle size can be used initially. The slurry of active, optional dispersant and modified polysaccharide is formed under ambient conditions with constant agitation for a period of from about 0.25 to about 2 hours. After a uniform mixture is formed, it is allowed to stand for 1–5 minutes to assure that no settling occurs and is then subjected to drying. The particle size of the resulting dried product can be further reduced, if necessary, by recrushing or pulverizing the dried product, after which it can be stored in suitable containers until ready for dilution to prepare a liquid spray, or it can be used as a concentrated paste or employed as a dust or in any other form desired by the formulator.

Reference is now had to the following Examples and Drawing which illustrate preferred embodiments of the invention or provide comparative data with matrices heretofore employed. However, the examples are not to be construed as limiting to the scope of the invention which is more broadly described above and defined in the appended claims.

Referring now to the accompanying drawing which graphically illustrates comparisons in starch dispersibility for 1. A 50/50% mixture of starch and PVP (polyvinylpyrrolidone)
2. Starch alone (control)
3. A 50/50% mixture of starch and VP (Vinyl pyrrolidone)/VA (vinyl acetate)copolymer
4. A 50/50% mixture of starch and VP/butene (90/10%) copolymer
5. A 50/50% mixture of starch and VP/DMAEMA (98/2%) copolymer
6. A 50/50% mixture of starch and VP/DMAEMA (80/20%) copolymer.

Matrices 1–6 were prepared in the following manner.

EXAMPLE 1

50/50 Starch/PVP* Matrix

A. A 16 oz. glass stoppered bottle was charged with 50 g of commercially available corn starch, 50 g of polyvinyl pyrrolidone (PVP K-30) and 250 g of deionized water and the bottle contents slurried by stirring in a mechanical stirrer for a period of one hour. The slurry was divided into 8 portions each of which was transferred to a 50 ml freezing jar. The jar and contents of each was precooled to −20° C. and maintained for one hour followed by freeze drying at −40° C. at a pressure ~0.1 mm Hg for a period of 16 hours in a commercial freeze-drier unit. The resulting solid deposit was collected and ground in a high speed centrifugal mill to average 200μ particle size and then dried in a vacuum oven at 50° C. at ~1 mm Hg for a period of 24 hours. The freeze-dried product was collected.

* polyvinyl pyrrolidone homopolymer

B. Several 2% solid suspensions of the above collected composition were prepared by suspending 1 g. of the matrix solid in 49 ml of deionized water and equal portions of the suspension at room temperature were then introduced into separate measuring cylinder tubes where they were held for varying holding periods ranging from 0 to 2 hours. After each period within the above time frame, the starch content and dispersion was determined by taking a 25 ml aliquot sample from the top of the cylinder and subjecting it for 15 minutes to centrifuging at 2500 RPM. The resulting separated solid was washed with water to dissolve water soluble polymer and the remaining suspension in the centrifuge tube was dried in a vacuum oven at 50° C. at about 1 mm Hg for a period of 24 hours. The dried starch recovered was weighed, the % dispersed was calculated (0.25 g. being 100% dispersion) and the results from each aliquot plotted on the accompanying graph, which, in this example, is represented as curve 1.

EXAMPLE 2

100% Starch Matrix

Part B of Example 1 was repeated except that 100% non-freeze dried corn starch was substituted as the matrix and the % dispersed starch over the same time periods was calculated and the results plotted on the graph and identified as curve 2.

EXAMPLE 3

50% Starch+40/60 Vinyl Acetate/N-vinyl Pyrrolidone Copolymer Matrix

Parts A and B of Example 1 were repeated except that N-vinyl pyrrolidone/Vinyl acetate copolymer was substituted as the polymer of the matrix. The dispersed starch over the same time periods was calculated and the results plotted on the graph and identified as curve 3.

EXAMPLE 4

50% Starch+50/50 N-Vinyl Pyrrolidone/Butene Copolymer Matrix

Parts A and B of Example 1 were repeated except that N-vinyl pyrrolidone/butene was substituted as the polymer of the matrix. The dispersed starch over the same time periods was calculated and the results plotted on the graph where it is identified as curve 4.

EXAMPLE 5

50% Starch+98/2 N-Vinyl Pyrrolidone/DMAEMA Copolymer Matrix

Parts A and B of Example 1 were repeated except that N-vinyl pyrrolidone/DMAEMA (dimethylamino ethylmethacrylate) was substituted as the polymer of the matrix. The dispersed starch over the same time periods was calculated and results plotted on the graph where it is identified as curve 5.

EXAMPLE 6

50% Starch+80/20 N-Vinyl Pyrrolidone/DMAEMA Matrix

Parts A and B of Example 1 were repeated except that the 80/20 VP/DMAEMA comonomer was substituted as the polymer of the matrix. The dispersed starch over the same time periods was calculated and results plotted on the graph where it is represented as curve 6.

In Examples 5 and 6 above, dimethylamino propyl-methacrylate can be substituted for DMAEMA to provide substantially similar starch dispersibility.

It is readily apparent that the amount of matrix dispersed and the stability of the resulting dispersion is astonishingly increased by several orders of magnitude when the polysaccharide is modified by the addition of hydrophilic-hydrophobic copolymer as opposed to modification with homopolymer. In the case of curves 5 and 6, the stability of the dispersion is more than quadrupled from 0.5 hour in curves 1 and 2 to more than 2 hours (the last observation reported).

COMPARATIVE EXAMPLE 7

Starch granule matrix containing metolachlor herbicide were prepared by adding 42.73 grams of corn starch to 5.04 grams of metolachlor and 52.24 mls deionized water while homogenizing with an IKA Ultra Turrax T-25 homogenizer equipped with a S-25 N 18 G size generator at ~20000 rpm. The resulting homogeneous mixture was then transferred to a covered porcelain dish and heated on a steam table at ~100° C. for 35 minutes after which it was allowed to cool to room temperature. The solid was too hard to be extruded.

EXAMPLE 8

Example 7 was repeated replacing 42.73 grams of starch and 52.24 mls of deionized water with a mixture of 38.46 grams of starch and 21.37 grams of a 20% solution of the copolymer of Example 5 (Copolymer 845) and using 35.14 mls deionized water. The resulting product (dough) was dried in a 50° C. vacuum oven at ~5 mm Hg until its consistency was hard enough for extruding. Periodic kneading was required while drying as the surface dried much faster than the center. The dough was then transferred to a basket type extruder (LCI Benchtop Granulator) with a 1 mm screen and extruded. The extrudate was then dried overnight at room temperature to yield constant granule size of 0.5 to 1 mm. This product possesses excellent sustained release of the active component.

EXAMPLE 9

Starch granules containing metolachlor herbicide and the copolymer of Example 5 (Copolymer 845) were prepared as in Example 8 but the amount of Copolymer 845 solution was increased to 43.70 grams and the starch and metolachlor was reduced to 26.21 and 3.88 grams respectively. 26.21 mls of deionized water was used. The resulting dough was extrudable as in Example 8 and possesses the same excellent sustained release properties for the active component.

It will be understood that the present compositions may contain additional additives in amount of from 0.01 up to 6% based on the total composition Such additives optionally employed in the composition include a non-ionic or anionic surf actant, a defoaming agent, a disintegrant, a film forming polymer and any component normally associated with the active chemical when supplied in a concentrate form, such as a hair or skin moisturizer, mollifying agent, coloring agent, etc.

It is also within the scope of this invention to employ many modifications and alterations which become apparent from the foregoing disclosure. For example, other comonomer species could be substituted or added to those described above provided that the hydrophilic-hydrophobic balance is maintained.

What is claimed is:

1. A free flowing particulate matrix suitable as a substrate for an active chemical which comprises polysaccharide infuse with a copolymer derived from a major amount of hydrophilic N-vinyl lactam monomer containing 4 to 8 ring carbon atoms, optionally substitued on the ring with $C_1$ to $C_4$ alkyl and a minor amount of a hydrophobic $C_1$ to $C_4$ alkyl amino, $C_1$ to $C_4$ alkyl-acrylate or methacrylate comonomer.

2. The matrix of claim 1 wherein said monomer is N-vinyl pyrrolidone or a mixture of N-vinyl pyrrolidone and another N-vinyl lactam containing 4 to 6 ring carbon atoms.

3. The matrix of claim 1 wherein said polysaccaride infuse with said copolymer is a particulate solid having an average diameter of from about 10 and about $350\mu$.

4. The matrix of claim 3 wherein said polysacharide infuse with said copolymer has an average diameter particle size of from about 15 to about $200\mu$.

5. The matrix of claim 1 wherein said copolymer is up to 2% crosslinked.

6. The matrix of claim 2 wherein at least one of said N vinyl lactam monomers is quaternized.

7. The matrix of claim 1 which contains between about 10 and about 90 wt. % polysaccharide and between about 90 and about 10 wt. % copolymer.

8. The matrix of claim 7 which contains between about 25 and about 75 wt. % polysaccharide and between about 75 and about 25 wt. % copolymer.

9. The matrix of claim 1 wherein said copolymer is the copolymer of N-vinyl pyrrolidone monomer and a comonomer selected from the group consisting of dimethylamino ethyl methacrylate and dimethylamino propyl methacrylate.

10. The matrix of claim 9 wherein the polysaccharide is starch.

11. The matrix of claim 1 wherein said N-vinyl lactam is N-vinyl pyrrolidone.

12. The matrix of claim 1 wherein said N-vinyl lactam is a mixture of N-vinyl pyrrolidone and N-vinyl caprolactam.

13. The matrix of claim 1 wherein said copolymer contains between about 60 and about 98.5 wt. % of said monomer.

14. The matrix of claim 1 wherein said copolymer contains between about 70 and about 95 wt. % of said monomer.

15. A free flowing particulate composition comprising a chemically active compound uniformly dispersed on a matrix of one of claims 2, 4, 8, 1 or 12.

16. The particulate composition of claim 15 wherein said chemically active compound is selected from the group consisting of a cleansing, pharmaceutical, agricultural, hair conditioning, skin conditioning and disinfecting chemicals.

17. The particulate composition of claim 15 which additionally contains from about 1 to about 20 wt. %, based on the active chemical, of an oxygen containing dispersant for said active chemical.

18. The particulate composition of claim 17 wherein said dispersant is selected from the group consisting of lignin sulfonate, naphthalene sulfonate/formaldehyde condensate, a sodium $C_1$ to $C_{18}$ succinate, a $C_1$ to $C_{18}$ sulfate, a sodium salt of an ethoxylated acrylate, a sodium salt of an ethoxylated methacrylate, a $C_1$ to $C_4$ alkyl vinyl ether/maleic acid half ester salt and a poly anionic polymer.

19. The composition of claim 15 which is applied to a substrate as a powder containing an effective chemically active amount of said active compound.

20. The composition of claim 15 which is applied to a substrate as a 2 to 50% aqueous solution containing an effective chemically active amount of said active compound.

* * * * *